(12) United States Patent
Sugita et al.

(10) Patent No.: US 8,267,079 B2
(45) Date of Patent: Sep. 18, 2012

(54) INHALER

(75) Inventors: Masaru Sugita, Tokyo (JP); Hiroshi Komatsu, Yokohama (JP); Hiroyuki Wada, Machida (JP); Yoshiyuki Fukumoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 590 days.

(21) Appl. No.: 12/504,459

(22) Filed: Jul. 16, 2009

(65) Prior Publication Data

US 2010/0024812 A1 Feb. 4, 2010

(30) Foreign Application Priority Data

Aug. 4, 2008 (JP) ................................. 2008-200448

(51) Int. Cl.
  *A61M 11/00* (2006.01)
(52) U.S. Cl. ............................... 128/200.14; 128/200.21
(58) Field of Classification Search .......... 128/200.14–200.23, 202.21, 203.12, 128/203.15–203.17, 203.23, 203.26–203.27, 128/204.17; *A61M 11/00*
See application file for complete search history.

(56) References Cited

U.S. PATENT DOCUMENTS

| | | | | | |
|---|---|---|---|---|---|
| 2,057,353 | A | * | 10/1936 | Whittemoore | ................ 392/395 |
| 2,462,129 | A | * | 2/1949 | Robinson | ................ 128/203.27 |
| 3,080,624 | A | * | 3/1963 | Weber | ................ 422/125 |
| 2008/0163869 | A1 | | 7/2008 | Nobutani et al. | ........ 128/200.23 |
| 2008/0190422 | A1 | | 8/2008 | Nobutani et al. | ........ 128/200.24 |
| 2009/0050139 | A1 | * | 2/2009 | Watanabe et al. | ........ 128/200.14 |
| 2009/0126722 | A1 | | 5/2009 | Sugita et al. | ............. 128/200.19 |
| 2009/0260624 | A1 | * | 10/2009 | Wada et al. | .............. 128/203.12 |
| 2009/0283094 | A1 | | 11/2009 | Hamano et al. | .......... 128/203.15 |
| 2010/0006094 | A1 | * | 1/2010 | Tsuchiya et al. | ......... 128/203.12 |
| 2010/0024814 | A1 | * | 2/2010 | Sugita et al. | ............. 128/203.14 |

FOREIGN PATENT DOCUMENTS

| | | |
|---|---|---|
| CN | 101111276 | 1/2008 |
| JP | H07-276616 | 10/1995 |
| JP | H09-141874 | 6/1997 |
| JP | 2006-304914 | 11/2006 |

OTHER PUBLICATIONS

Chinese Office Action dated Jun. 22, 2011, issued in the Chinese counterpart of the present application, Chinese Patent Application No. 200910160193.6, including English translation.

* cited by examiner

*Primary Examiner* — Oren Ginsberg
(74) *Attorney, Agent, or Firm* — Fitzpatrick, Cella, Harper & Scinto

(57) ABSTRACT

A cartridge having an ejection head for ejecting medicine and a reservoir as integral parts thereof is provided with an electric connection section on a lower surface of a junction forming section thereof to be brought into contact with an inhaler body. As the cartridge is put into the inhaler body and secured to the latter by means of a cartridge fixing member, the electric connection section of the cartridge is brought into contact with an electric connection section arranged on a top surface of a cartridge mounting section of the inhaler body to establish electric connection between the cartridge and the inhaler body.

2 Claims, 12 Drawing Sheets

FIG. 3A
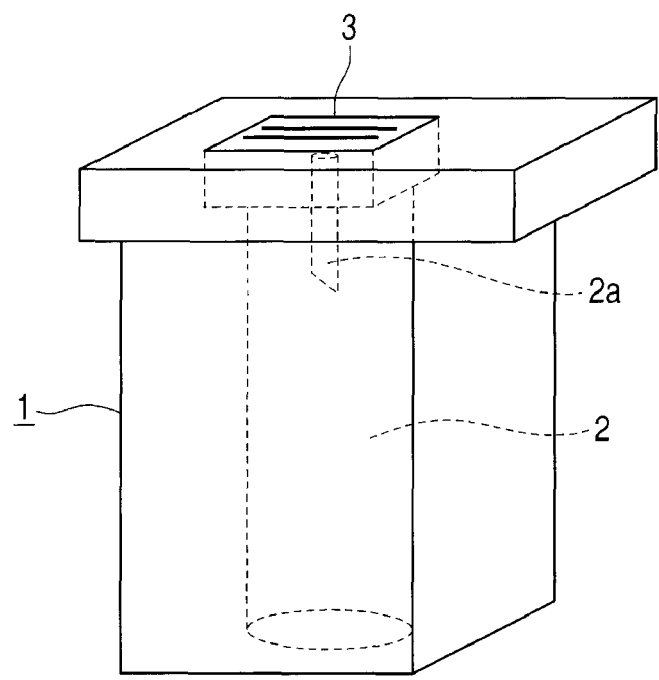
FIG. 3B  FIG. 3C  FIG. 3D
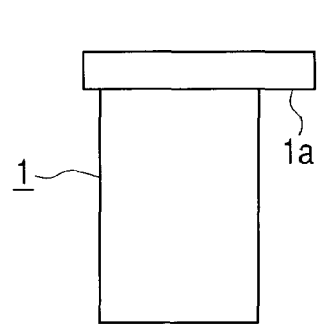 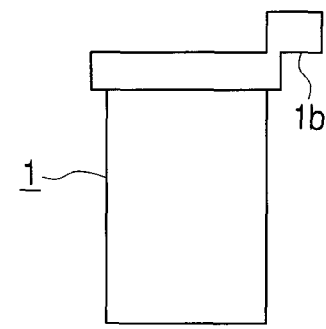 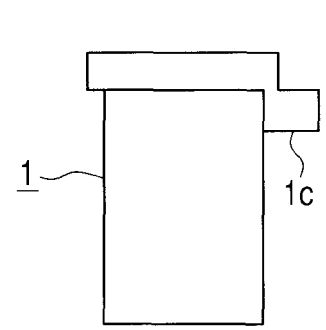

INHALER

BACKGROUND OF THE INVENTION

1. Field of the Invention

The present invention relates to an inhaler for ejecting medicine as liquid droplets and causing the user to inhale it.

2. Description of the Related Art

There are various methods of administering medicine to a patient's body including oral administration, injection by needle, application to the exterior of the body, and the use of a patch, and various devices and systems have been developed for each of these methods. Additionally, many electric devices have been developed as medical equipment as a result of the advancement of science and technology in recent years to make it possible to realize what has been difficult to achieve by mechanical means.

Many varieties of electrical medical equipment are diagnostic devices, while devices for administering medicine also exist, one example being nebulizers. The nebulizer has a vibrator as source of atomization of medicine and electric power is required for it as power source.

By observing devices for administering medicine particularly from the viewpoint of repetitive administration of medicine and replacement, it will be found that a nebulizer is so designed that a package of medicine that is independent of the nebulizer is moved into the device and subsequently atomized so that the user may inhale the medicine as he or she breathes. A package of medicine needs to be provided for each use of the nebulizer. The vibrator that is the source of atomization of medicine is operated repetitively and needs to be periodically cleaned to keep it in a sanitary condition. In other words, a nebulizer is not a particularly convenient system from the user's viewpoint.

On the other hand, such problems have already been solved in some other technical fields. For instance, a simple arrangement is provided for ink-jet printers so as to simplify the replacement operation. More specifically, a cartridge structure formed by integrally combining an ejection head for ejecting ink for printing that requires electric power, an electric connection section for supplying electric power and a container for storing ink is provided for use with an ink-jet printer. While the printer main body normally has a long service life, the ink supply needs to be replenished frequently. If an ejection head is incorporated into the main body from the beginning and develops a problem, it is a cumbersome, costly and time-consuming operation to repair the ejection head. If, on the other hand, an ejection head is provided as a replaceable part, the problem can be solved with ease.

When such an integrated cartridge is adopted, it needs to satisfy the requirements that the operation of removably putting the cartridge in position relative to printer main body should be easy and visually recognizable and the parts thereof that are directly related to the operation should be very strong, durable and dimensionally precise. For example, Japanese Patent Application Laid-Open Nos. H07-276616 and H09-141874 disclose techniques developed from this viewpoint.

More specifically, Japanese Patent Application Laid-Open No. H07-276616 relates to an arrangement of securing an integrated cartridge to a printer and subsequently rotating the cartridge so as to rigidly hold it in position in order to electrically energize it, while bringing electric connection terminals into contact with each other simultaneously.

Japanese Patent Application Laid-Open No. H09-141874 relates to a spacer having dimensions adapted to isolate the electric connection sections of an ejection head in order to reduce the number of parts to be replaced when the ejection head is replaced and make the electric connection sections contact each other appropriately so as to establish a stable electric connection.

As pointed out above, an integrated cartridge needs to meet all the requirements that the operation of removably putting the cartridge in position relative to printer main body should be easy and visible and the parts thereof that are directly related to the operation should be very strong, durable and dimensionally precise in order to satisfy the user.

However, the cartridge and the printer main body have a plurality of parts that need to be linked or brought into contact in order to meet a variety of functional requirements they have. If they have problems in terms of structure and/or construction for realizing such functions simultaneously including establishing a plurality of contacts, the fixed parts of the cartridge can be damaged and degraded while the electric connection terminals may be worn and degraded.

While the linking and contacting units can be isolated to avoid the above identified problem, the number of operations that the user needs to perform will then be increased, and one or more additional mechanisms and spaces are required to consequently make the main body more complex and larger. Furthermore, the functions of a system that requires a cartridge to be replaced frequently should be reliable, reproducible and visually recognizable to the user.

SUMMARY OF THE INVENTION

In view of the above-described circumstances, the object of the present invention is therefore to provide an inhaler to which a cartridge having an ejection head and a reservoir can be removably fitted and electrically connected with ease in a visually recognizable manner and which can operate accurately and durably.

According to the present invention, the above object is achieved by providing an inhaler for ejecting medicine and causing a user to inhale it, the inhaler including: a cartridge having an ejection head for ejecting medicine and a reservoir; an inhaler body equipped with a cartridge mounting section for mounting the cartridge thereon; a junction forming section arranged at the cartridge so as to be brought into contact with the cartridge mounting section of the inhaler body; a cartridge fixing member for fixing the cartridge on the inhaler body; a first electric connection section arranged at the junction forming section of the cartridge; and a second electric connection section arranged at the cartridge mounting section of the inhaler body to be held in contact with the first electric connection section in order to supply electric power to the ejection head. The cartridge fixing member is adapted to connect the first electric connection section to the second electric connection section by fixing the junction forming section of the cartridge to the cartridge mounting section of the inhaler body.

In an inhaler according to the present invention, the cartridge can be fitted and electrically connected to the inhaler body with ease. Additionally, since the electric connection sections are designed to be scarcely worn and degraded, the service life of the inhaler is prolonged and the parts of the inhaler require replacement less frequently.

This is because the first electric connection section and the second electric connection section are made to abut and contact each other in the direction in which the cartridge is mounted on the inhaler body so that the terminals and the contacts of the electric connection sections may be worn less. Additionally, since the cartridge is electrically connected to the inhaler body in an operation of being mounted on the latter, the overall operation is easy and the contacts can be arranged respectively at visually highly recognizable positions.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 3A, 3B, 3C and 3D are schematic views of the cartridge of FIG. 1, FIG. 3A is a schematic perspective view of the cartridge, illustrating the internal structure thereof with broken lines, FIG. 3B is a schematic perspective view of the cartridge, and FIGS. 3C and 3D are schematic lateral views of two cartridges formed by modifying the cartridge of FIG. 1.

FIG. 4A is a schematic perspective view of the cartridge, and FIG. 4B is a schematic perspective view of the cartridge turned to lie on one of the lateral sides thereof in order to illustrate the electric connection section.

DESCRIPTION OF THE PREFERRED EMBODIMENTS

Preferred embodiments of the present invention will now be described in detail in accordance with the accompanying drawings.

Figure 1:
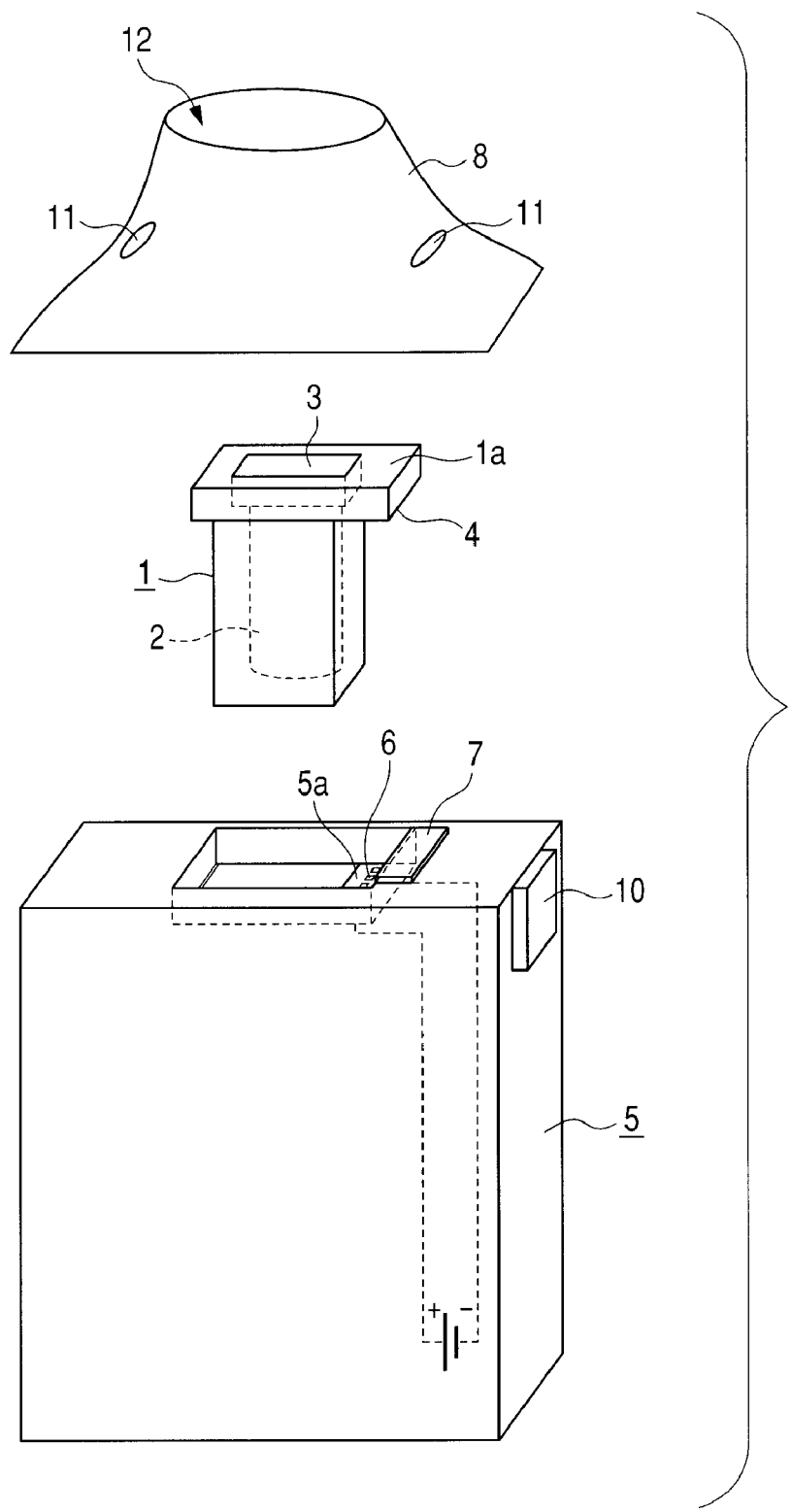
FIG. 1 is an exploded schematic perspective view of the first embodiment of inhaler according to the present invention.
Figure 2:
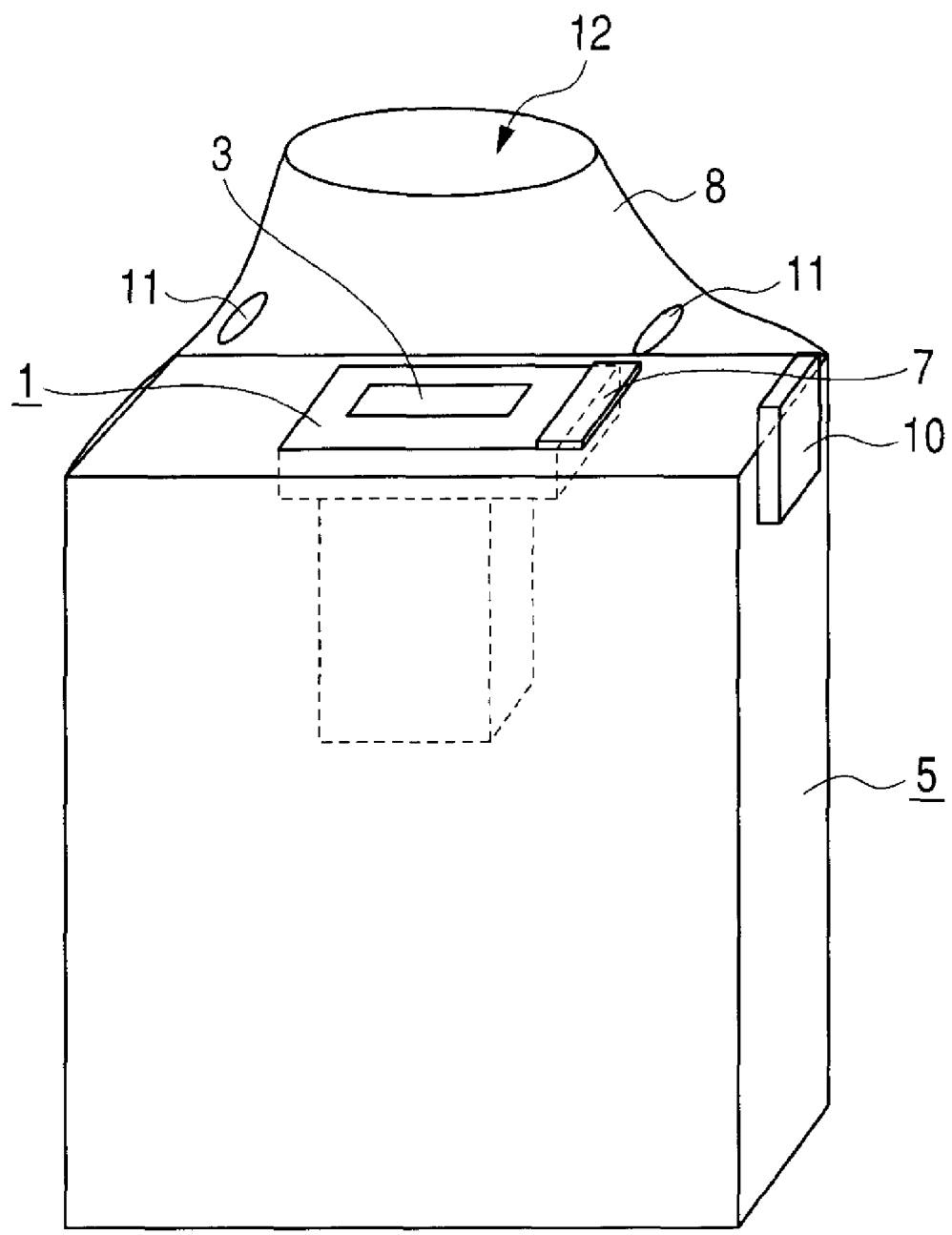
FIG. 2 is a schematic perspective view of the assembled inhaler of FIG. 1 with a see-through view of the inhalation piece thereof.

FIG. 1 is an exploded schematic perspective view of an embodiment of inhaler according to the present invention. FIG. 2 is a schematic perspective view of the assembled inhaler of FIG. 1. Cartridge 1 has a reservoir 2 for storing medicine to be ejected, an ejection head 3 for ejecting medicine and a first electric connection section 4 for supplying power to the ejection head 3 among others. Inhaler body 5 has a second electric connection section 6, a cartridge fixing member 7 and so on. The inhaler further has an inhalation piece 8 to be held by a user at his or her mouth or nose to inhale the ejected medicine and one or more inlet ports 11 are arranged at the inhalation piece 8 so as to form an air flow in the inhalation piece 8 by means of which the user inhales the ejected medicine. Electric power can be supplied from the inhaler body to the ejection head 3 as the first electric connection section of the cartridge 1 and the second electric connection section 6 of the inhaler body 5 are electrically brought into contact with each other. "Electric power" as used herein may refer to DC, AC or a pulse-shaped drive signal for driving the ejection head, a DC voltage or a steady state electric current.

An air flow is generated and directed from the inlet ports 11 toward suction port 12 as the user holds the inhalation piece 8 in his or her mouth and breathes in. Then, as medicine is ejected into the air flow path, medicine is carried toward the inhalation piece 8 by the air flow that operates as a medicine carrier, and is administered to the user. The suction port 12 may be so profiled that the user inhales medicine through the mouth or through the nose.

The inhalation piece may have any appropriate profile. More specifically, it may be box-shaped or alternatively it may have a curved profile. Preferably, however, the part of the inhalation piece that is brought into contact with the user is designed on the basis of human engineering and the remaining part is designed so as not to influence the air flow and the mist.

The inhaler body may be provided with a CPU (control section) that controls the operation of the entire inhaler including the operation of driving the ejection head. Furthermore, the inhaler body may be provided with a sensor for detecting an air flow and also the difference between the atmospheric pressure and the air pressure that is produced in the inside of the air flow path as the user breathes and the inhaler may be so designed as to transmit a drive signal representing the air flow and the pressure difference that are detected by the sensor from the control section to the ejection head so as to synchronously start ejecting medicine according to the signal. Still additionally, the inhaler body may also be provided with a display section for displaying information that makes the user visually recognize the operation he or she is doing on the inhaler, the condition of the current ejection of medicine and so on.

The inhaler is provided with a power supply switch (not illustrated) and the system of the inhaler is made ready for various operations according to an operation signal transmitted from the power supply switch. As for power supply, a battery is arranged in the inhaler body and power is supplied from it to various relevant components by way of electric wiring in order to operate the ejection head and the system. Any type of battery may be employed for the purpose of the present invention so long as it can supply power at a desired rate with a desired level of voltage and a desired level of electric current. The inhaler may be provided with a power supply port (not illustrated) so that power may be supplied to it from an external power source.

As illustrated in FIG. 1, the cartridge 1 includes an electric connection section 4, a reservoir 2 for storing (containing) medicine and an ejection head 3 for atomizing medicine and the reservoir and the ejection head can be linked to each other in the inside of the cartridge. In short, the cartridge 1 is an integrated type cartridge. As illustrated in FIG. 2, the inhaler becomes ready to operate when the cartridge 1 is mounted on the inhaler body 5 and subsequently the inhalation piece 8 is mounted on top of the cartridge 1 and secured to the inhaler body 5 with the cartridge 1 by means of the inhalation piece fixing member 10.

As illustrated in FIG. 3A, a medicine flow path is formed in the cartridge 1 between the ejection head 3 having a nozzle array for ejecting medicine and the reservoir 2 by means of a communication needle 2a so that medicine is supplied from the reservoir 2 to the ejection head 3.

Figure 4A:
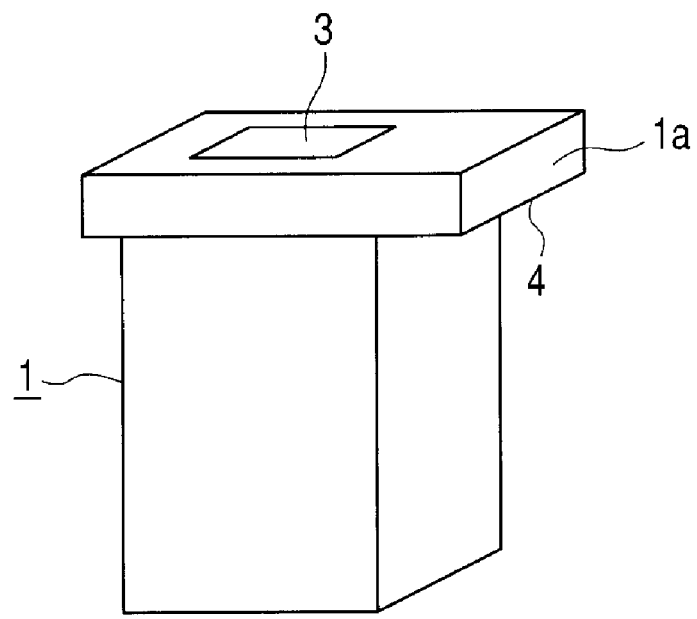
FIGS. 4A and 4B are schematic external views of the cartridge of FIG. 1.
Figure 4B:
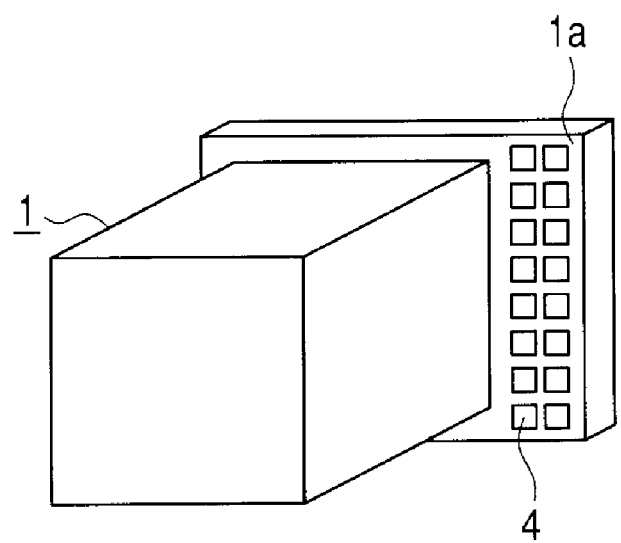

As illustrated in FIGS. 4A and 4B, the first electric connection section 4 for supplying electric power to the cartridge 1 is arranged at the junction forming section 1a that projects from the lateral sides of the cartridge 1. As the cartridge 1 is put into the inhaler body 5 and rigidly secured to the inhaler body 5 by means of the cartridge fixing member 7, the electric connection section 4 is forced to abut the second electric connection section 6 arranged at the cartridge mounting section 5a of the inhaler body 5 so as to establish electric connection between the cartridge 1 and the inhaler body 5. For the purpose of the present invention, "the junction forming section arranged at the cartridge" refers to an appropriate part of the surface of the cartridge 1 that is brought into contact with the inhaler body 5 when the cartridge is mounted on the inhaler body 5. On the other hand, the term "cartridge mounting section of the inhaler body" 5 refers to the part thereof that is brought into contact with the cartridge 1 when the cartridge 1 is mounted on the inhaler body 5. For the purpose of the present invention, the first electric connection section 4 is arranged at the junction forming section of the cartridge, while the second electric connection section 6 is arranged at the cartridge mounting section of the inhaler body. The electric connection sections 4 and 6 are arranged respectively at the junction forming section and the cartridge mounting section so as to establish electric connection between the cartridge 1 and the inhaler body 5 when the cartridge 1 is mounted on the inhaler body 5 and rigidly secured there.

Thus, since the electric connection sections 4 and 6 are so formed as to abut and contact each other in the direction in which the cartridge 1 is mounted on the inhaler body 5, the electric connection sections 4 and 6 are hardly worn and degraded and hence connection failure and other troubles are minimized if the cartridge 1 is removably mounted on the inhaler body 5 frequently. The electric connection sections 4 and 6 can be formed by using any material so long as a desired level of electric conductivity is realized. The electric connection sections 4 and 6 may be provided with projections and recesses. For the purpose of the present invention, the direction in which the cartridge 1 is mounted on the inhaler body 5 refers to the direction in which the cartridge 1 moves relative to the inhaler body 5 when the cartridge 1 is mounted. It is the lengthwise direction in FIG. 1.

The electric connection section of the cartridge is preferably arranged at a position close to the ejection head. A long wiring distance is disadvantageously required when the electric connection section of the cartridge is separated from the ejection head by a large distance.

Preferably, the electric connection section of the cartridge is formed by a plurality of terminals, all of which terminals are arranged on a same plane. Preferably, the plane where all the terminals of the electric connection section are arranged is perpendicular to the direction in which the cartridge is removably mounted on the inhaler body.

Preferably, a projecting section is arranged to project from the lateral sides of the cartridge so as to extend the plane where the ejection head is placed and the projection section is provided with the electric connection section. With this arrangement, both the cartridge and the inhaler body can be made to show a simple structure and the electric connection sections can be arranged at respective positions that are visually highly recognizable to the user so that the user can make sure with ease that electric connection is established between the cartridge and the inhaler body and the cartridge is mounted in position. Preferably, the terminals (contact pins) of the electric connection section are arranged on the flat projecting section that projects from the cartridge in the directions perpendicular to the direction in which the cartridge is put into the inhaler body as seen from FIGS. 3B through 3D. Preferably, the terminals are arranged on the rear side of the projecting section that is opposite to the side where the ejection head 3 is formed. The projecting section is formed integrally with the member to which the ejection head 3 is secured or that is arranged around the ejection head 3 and extends laterally from the lateral sides of the ejection head 3.

As illustrated in FIG. 3B, the projection section of the cartridge 1 having the junction forming section 1a where the electric connection section 4 is arranged projects from the lateral sides of the main body of the cartridge 1. The projecting section may show a profile selected from a variety of different possible profiles so long as it projects in the vicinity of the ejection head 3. For example, FIG. 3C illustrates an instance where a junction forming section 1b is formed on the bottom surface of the part of a projecting section whose top surface is displaced toward the inhalation piece from the plane of the cartridge 1 where the ejection head is arranged. FIG. 3D illustrates an instance where a junction forming section 1c is formed on the bottom surface of the part of a projecting section whose top surface is displaced conversely toward the inside of the inhaler body 5. The first electric connection section 4 is placed at a position remote from the surfaces of the cartridge cabinet in each of these instances.

The instance where a junction forming section 1b is formed on the bottom surface of the part of a projecting section whose top surface is displaced toward the inhalation piece from the plane of the cartridge 1 where the ejection head is arranged provides an advantage that the user can visually recognize the established electric connection very easily, whereas the instance where a junction forming section 1c is formed on the bottom surface of the part of a projecting section whose top surface is displaced conversely toward the inside of the inhaler body 5 provides an advantage that the cartridge can be secured to the inhaler body very reliably.

Figure 5A:
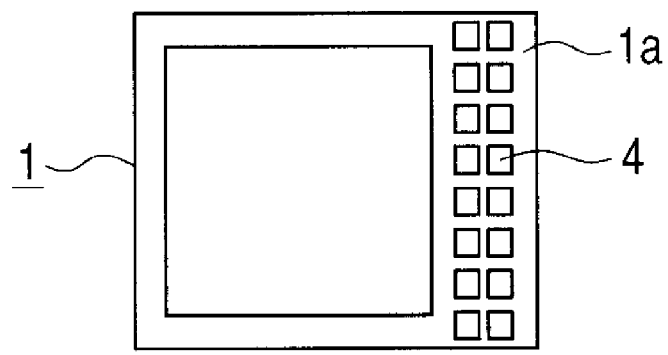
FIGS. 5A and 5B are a schematic view of the electric connection section of the cartridge and a schematic view of the electric connection section of the inhaler body.
Figure 5B:
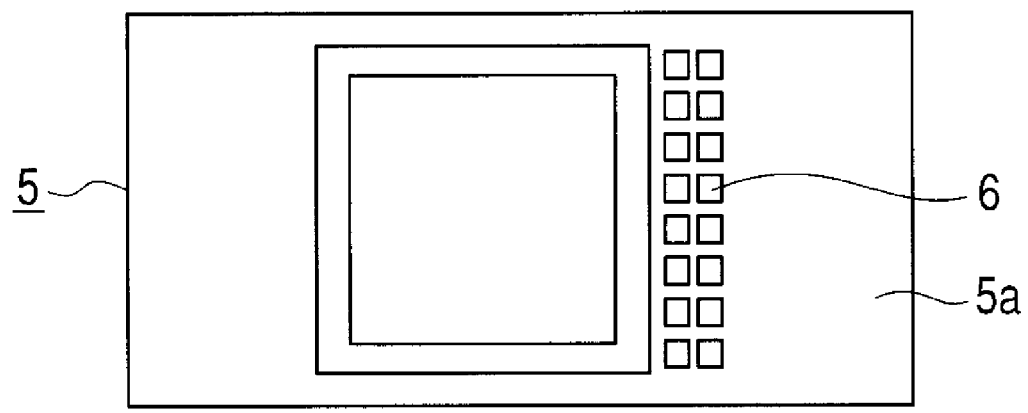
Figure 6:
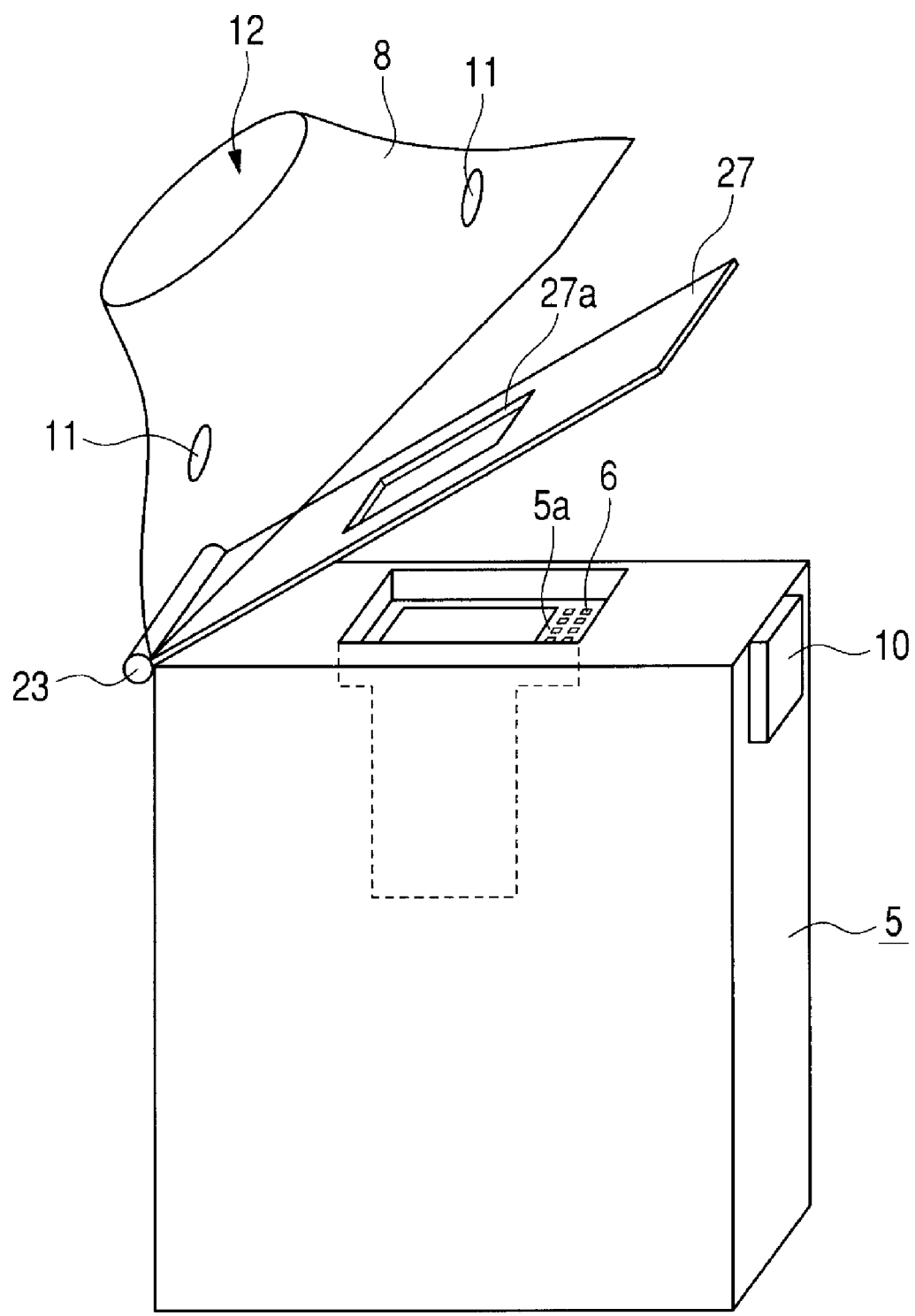
FIG. 6 is an exploded schematic perspective view of the second embodiment of inhaler according to the present invention.
Figure 7:
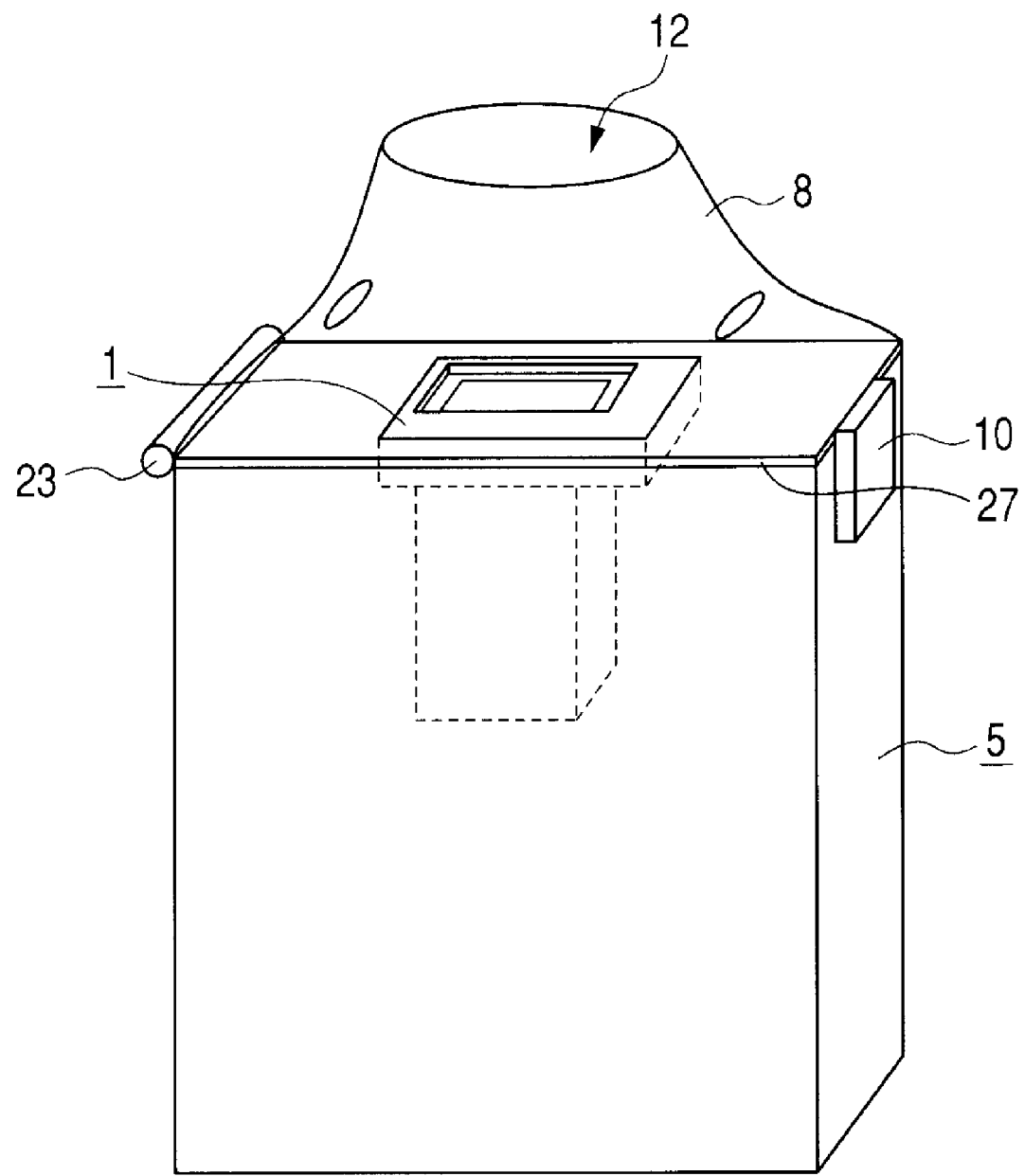
FIG. 7 is a schematic perspective view of the assembled inhaler of FIG. 6 with a see-through view of the inhalation piece thereof.

As illustrated in FIGS. 5A and 5B, the electric connection section 4 of the cartridge and the electric connection section 6 of the inhaler body that are arranged vis-à-vis and contact each other are arranged at suitable respective positions in a suitable manner according to the projecting profile of the junction forming section 1a of the cartridge 1.

The cartridge fixing member 7 operates to secure the cartridge 1 to the inhaler body 5. Any generally available unit may be used for the cartridge fixing member 7 so long as it can reliably secure the cartridge 1 to the inhaler body 5. For example, it may be a physical unit such as a pawl or a stoppers, a unit that can bond the cartridge 1 to the inhaler body 5 with ease or a non-contact unit such as magnetic power.

The cartridge 1 is put into and rigidly secured to the inhaler body 5 by the cartridge fixing member 7. At this time, the electric connection section 4 of the cartridge 1 contacts the electric connection section 6 of the inhaler body 5 and the contact is securely maintained by the cartridge fixing member 7 to make the inhaler operational.

The reliability of the operation of the inhaler is improved by the scheme that does not electrically energize inhaler when the cartridge 1 is put into the inhaler body 5 but electrically energizes the inhaler only when the cartridge 1 is rigidly secured to the inhaler body by the cartridge fixing member 7.

This scheme can be realized by arranging a restitutive member (not illustrated) such as a spring in the space in the inhaler body for receiving a cartridge 1. With such an arrangement, the inhaler is not electrically energized when the cartridge 1 is put into the inhaler body 5 but electrically energizes only when the cartridge 1 is forced into the space against the restitutive member and rigidly secured to the inhaler body by the cartridge fixing member 7.

As illustrated in FIG. 2, the first electric connection section 4 of the cartridge 1 and the second electric connection section 6 of the inhaler body are electrically connected to each other in the state where the cartridge 1 is mounted on and secured to the inhaler body 5 and the inhaler piece 8 is fitted in position.

Each of the electric connection sections has a plurality of terminals and each of the terminals thereof needs to be held in touch with and connected to their counterparts of the other electric connection section appropriately.

Additionally, appropriate force needs to be exerted to rigidly secure the oppositely disposed electric connection sections to each other and maintain the electric connection between them. The force is applied when the cartridge is secured to the inhaler body and maintained as the cartridge is held in position by the cartridge fixing member. A spacer may be provided in order to improve the accuracy more.

In an inhaler according to the present invention, the medicine ejection head (ejection head) has an appropriate ejection energy generating element. The ejection energy generating element may be an electrothermal transducer that applies thermal energy to medicine or an electro-mechanical transducer that applies mechanical energy to medicine. A thermal jet system for applying thermal energy to medicine by means of an electrothermal transducer and causing it to jet out from the ejection port or a system using an electro-mechanical transducer (e.g., a piezoelectric element) to apply mechanical energy to medicine and causing it to jet out under the vibration pressure of the electro-mechanical transducer may be used for the purpose of the present invention. The system to be used for an inhaler according to the present invention may be selected depending on the type of medicine.

When a thermal jet system is employed, individual liquid ejection units can be made to show a high level of dimensional accuracy and reproducibility in terms of the bore of the ejection port, the calories of the thermal pulse to be used for ejecting medicine, the size of the electrothermal transducer, which may typically be a micro-heater, etc. Therefore, the size distribution of liquid droplets can be confined to a small and narrow range. Additionally, a thermal jet type ejection head can be manufactured at low cost and hence can find applications in small apparatus that require the ejection head to be replaced frequently. Thus, a thermal jet type ejection system is preferable particularly when the medicine inhaler is required to be portable and convenient for use.

For the purpose of the present disclosure, the term "medicine" encompasses not only medicinal compounds that provide pharmaceutical and physiological effects but also tasty and fragrant ingredients, aromatics, dyes and pigments. Additionally, for the purpose of the present disclosure, the medicine may be a liquid or a powder.

For the purpose of the present disclosure, "medicinal liquid" refers to liquid medicine and liquid media that contain medicine. The medicinal liquid may contain any additive(s). As for the state of the solid (if any) contained in the liquid, it may be dissolved, dispersed, emulsified, suspended or slurried. Preferably, it may exist in the liquid in a uniform fashion.

When medicinal liquid is employed as medicine, the liquid's major medium is preferably water or an organic compound. It is more preferably water from the viewpoint that the medicinal liquid is administered to a living body.

An inhaler according to the present invention can find various applications. Medicine can be administered by means of an inhaler according to the present invention by way of the mouth or the nose of a user having a locally diseased respiratory organ or a diseased circulatory system of the entire body. Additionally, a particular site in the user's body can be targeted. Respiratory diseases that can be treated by means of an inhaler according to the present invention include asthma and chronic obstructive lung diseases, whereas diseases of the circulatory system of the entire body include diabetes mellitus.

Medicinal compounds that can be used for the purpose of the present invention include low molecular weight compounds and polymers such as peptides and proteins.

Example 1

FIG. 1 through FIGS. 5A and 5B schematically illustrate the first embodiment of inhaler according to the present invention. The cartridge 1 includes a reservoir 2, an ejection head 3 and a first electric connection section 4 for supplying power. As illustrated in FIG. 3A, the reservoir 2 and the ejection head 3 communicate with each other by way of a communication needle 2*a* in the cartridge so that medicine is supplied from the reservoir 2 to the ejection head 3.

An inhalation piece 8 to be used by the user to inhale medicine is mounted to the inhaler body 5 while the cartridge 1 is mounted in the inside of the inhalation piece 8.

As illustrated in FIGS. 5A and 5B, the inhaler body 5 has a cartridge mounting section 5*a* on which the cartridge 1 is mounted and a second electric connection section 6 and a restitutive member, which is described above, are arranged there. As the cartridge 1 is rigidly secured to the inhaler body 5 by means of the cartridge fixing member 7, the first electric connection section 4 of the cartridge 1 is brought into contact with the second electric connection section 6 of the inhaler body 5 to establish an electric circuit.

Then, as a result, power can be supplied to the ejection head 3 and related information can be transmitted to it. In short, electric power is reliably supplied to the cartridge 1 once the cartridge 1 is properly mounted, whereas no electric power is supplied to the cartridge so long as the cartridge is not properly mounted.

The second electric connection section 6 is arranged on the outer surface of the inhaler body 5 so that it can be visually recognized with ease by the user. Thus, the user can visually confirm that the cartridge 1 is properly mounted and electric connection is established between the cartridge and the inhaler body to provide the inhaler with an improved degree of reliability. To rigidly secure the cartridge 1 to the inhaler body 5, the cartridge fixing member 7 is moved from the position illustrated in FIG. 1 to the position illustrated in FIG. 2.

As illustrated in FIGS. 4A and 4B, the first electric connection section 4 is arranged on the rear surface of the projecting section of the cartridge 1 whose top surface is substantially flush with the top surface of the ejection head 3 arranged at the top side of the cartridge 1. As illustrated in FIGS. 5A and 5B, when the cartridge 1 is mounted on and rigidly secured to the inhaler body 5, the first electric connection section 4 is electrically connected to the second electric connection section 6 that comes to be arranged in front of it.

Example 2

FIGS. 6 and 7 schematically illustrate the second embodiment of inhaler according to the present invention. The second embodiment of inhaler includes a cartridge fixing member 27 having an opening 27a so as to surround the ejection surface of cartridge 1 and rigidly secure the cartridge 1 to the inhaler body 5. The cartridge 1, the inhaler body 5 and the inhalation piece 8 of this embodiment are the same as their counterparts of the first embodiment and hence denoted respectively by the same reference symbols and will not be described any further.

The cartridge fixing member 27 is supported at an end thereof by the inhaler body 5 so as to be able to turn at rotary section 23. The cartridge 1 is mounted on the inhaler body 5 and then the cartridge fixing member 27 is turned onto the cartridge to rigidly secure the cartridge in place. Then, the cartridge fixing member 27 contacts the cartridge 1 near the ejection head 3. Thus, the cartridge 1 is rigidly secured by the cartridge fixing member 27 and the inhalation piece 8 is rigidly secured by an inhalation piece fixing member 10 at the same time. The inhalation piece fixing member 10 may be provided separately relative to the inhaler body 5.

Figure 8:
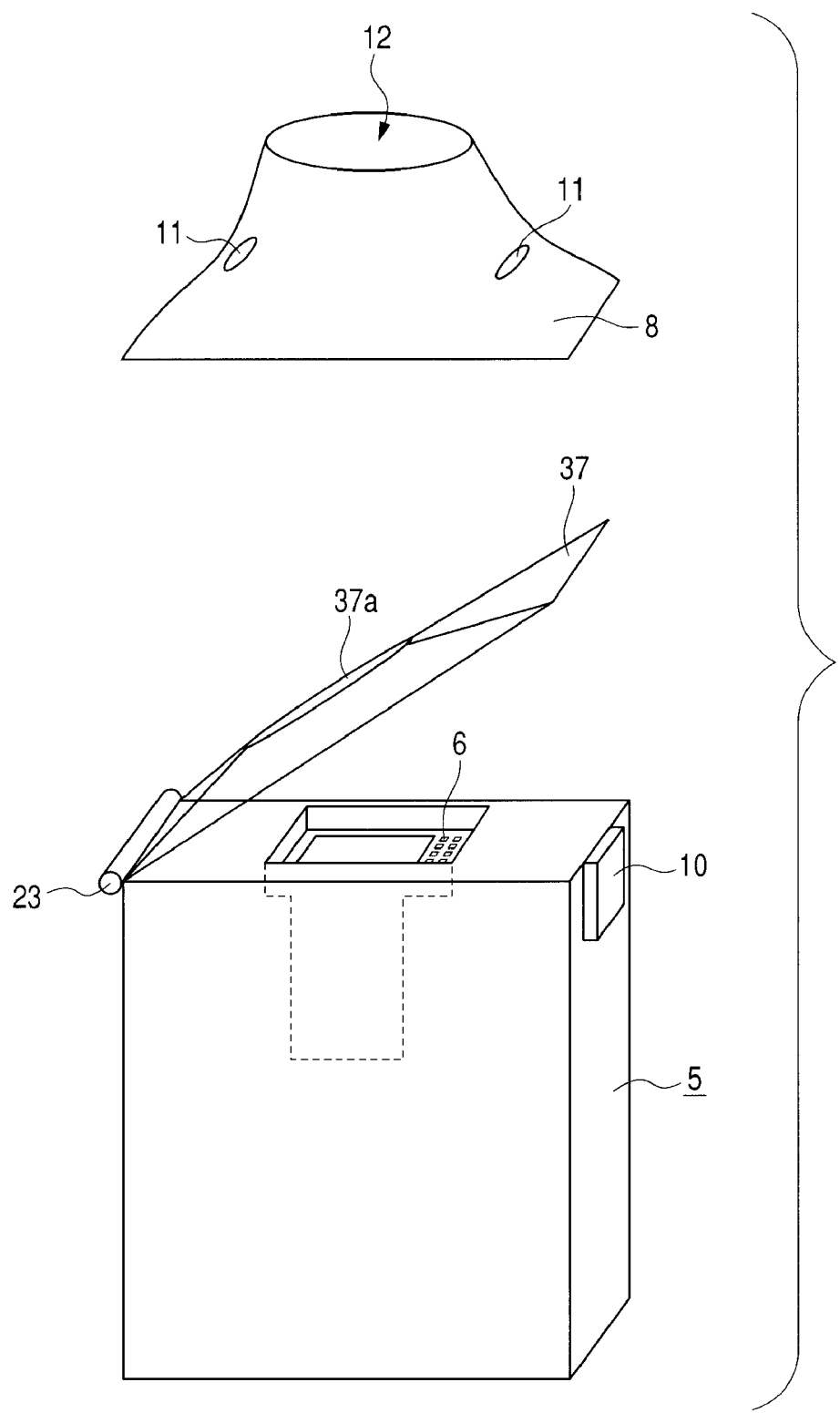
FIG. 8 is an exploded schematic perspective view of an inhaler formed by modifying the second embodiment of inhaler.
Figure 9:
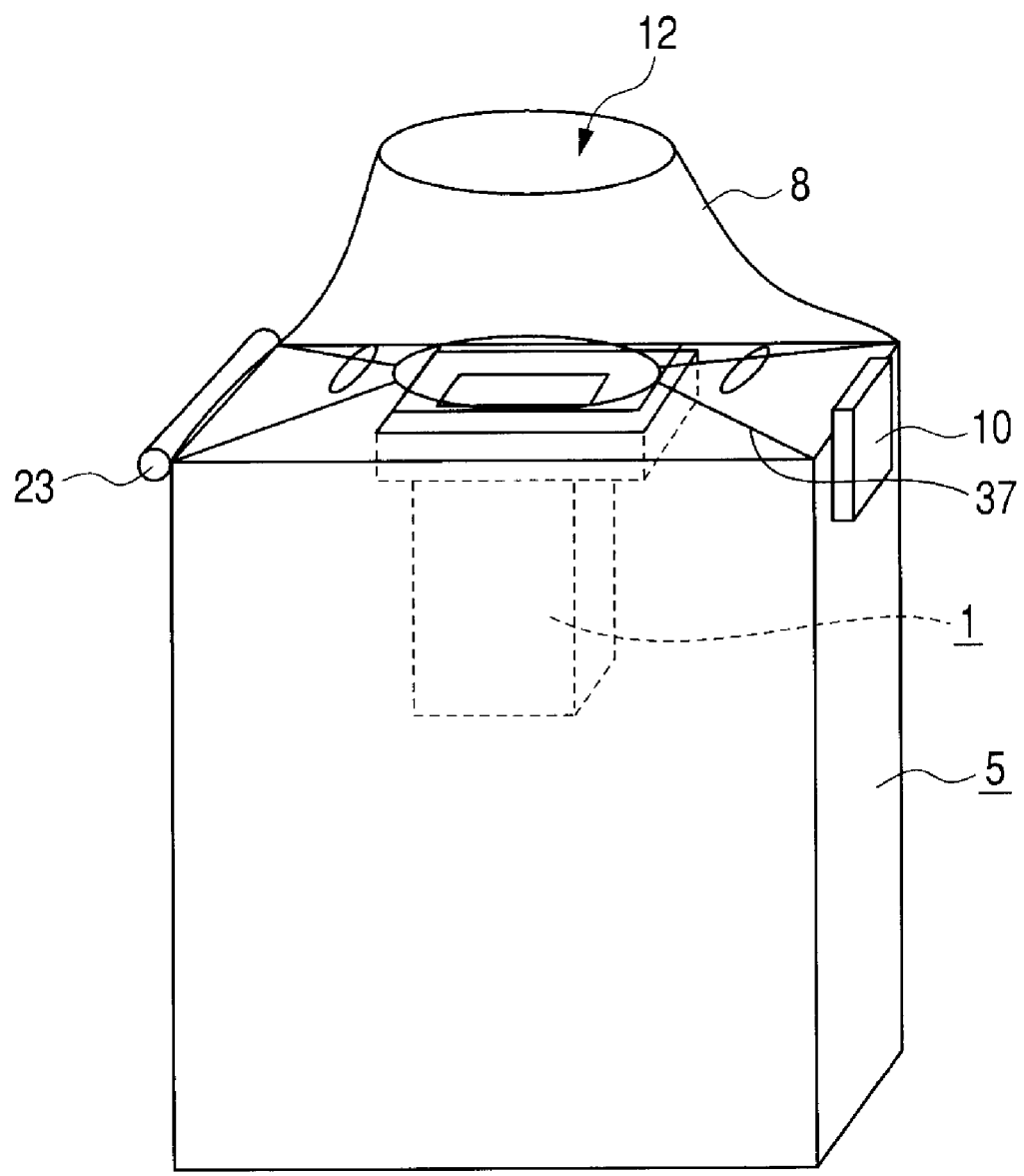
FIG. 9 is a schematic perspective view of the assembled inhaler of FIG. 8 with a see-through view of the inhalation piece thereof.
Figure 10:
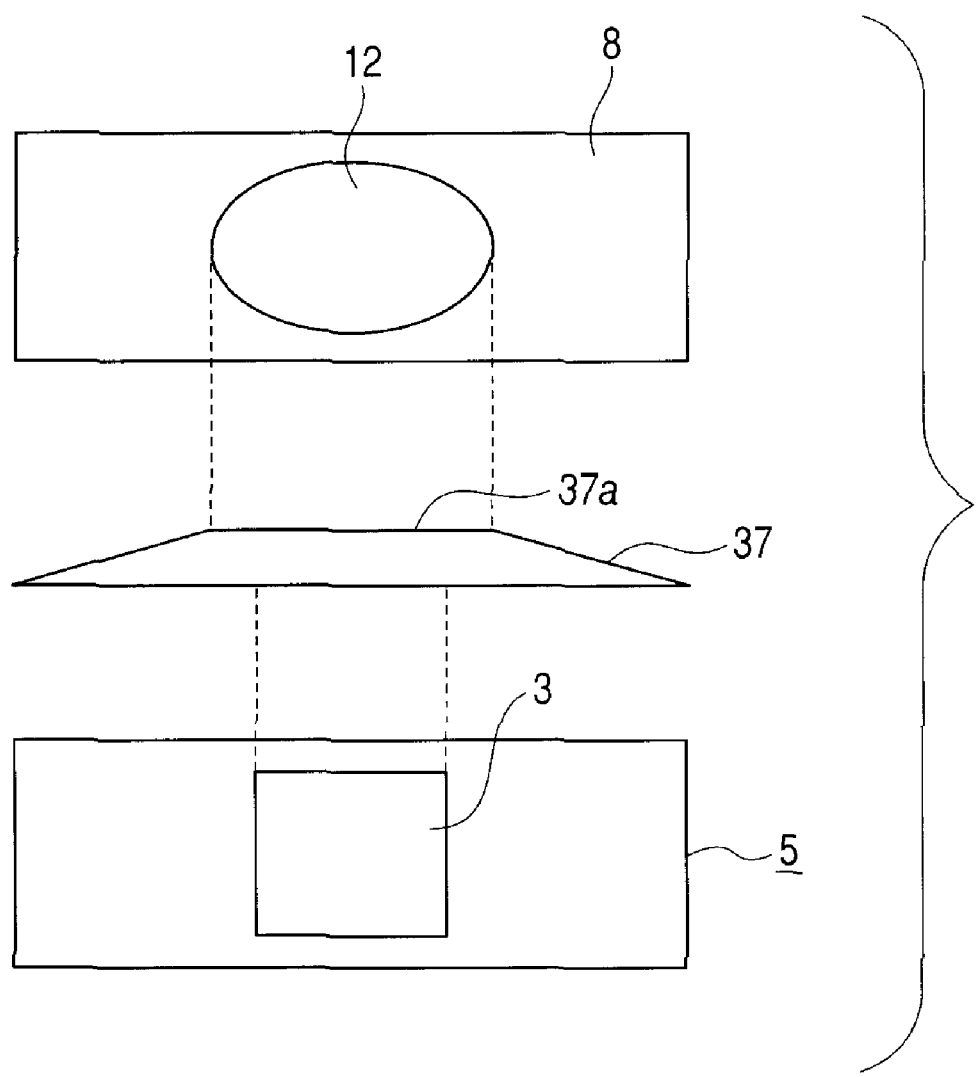
FIG. 10 is a schematic illustration of the relationship between the cartridge mounting section and the opening of the inhaler of FIG. 8.

FIGS. 8 and 9 schematically illustrate an inhaler formed by modifying the inhaler of the second embodiment. The cartridge fixing member 37 of this modified embodiment is made to show a profile that resembles the profile of the inhalation piece 8 in order to make the cartridge fixing member 37 having an opening 37a to be bound to the inhaler piece 8 and the inhaler body 5 more reliably with no gap separating them and generate a desired air flow. An arrangement that makes the cartridge fixing member form part of the air flow path is highly desirable. As illustrated in FIG. 10, the elliptic part of the cartridge fixing member 37 operates as window at the side of the inhaler piece while the rectangular part at the bottom of the cartridge fixing member 37 operates as window for the ejection head 3. The positional and dimensional relationship between the elliptic part and the rectangular part is so selected as to exert no influence on the ejection performance of the inhaler and the edges are so designed as to make the cartridge fixing member 37 snugly match the inhalation piece 8. The edges may be linear or not continuous and may be formed by straight lines or one or more curved lines.

Example 3

Figure 11:
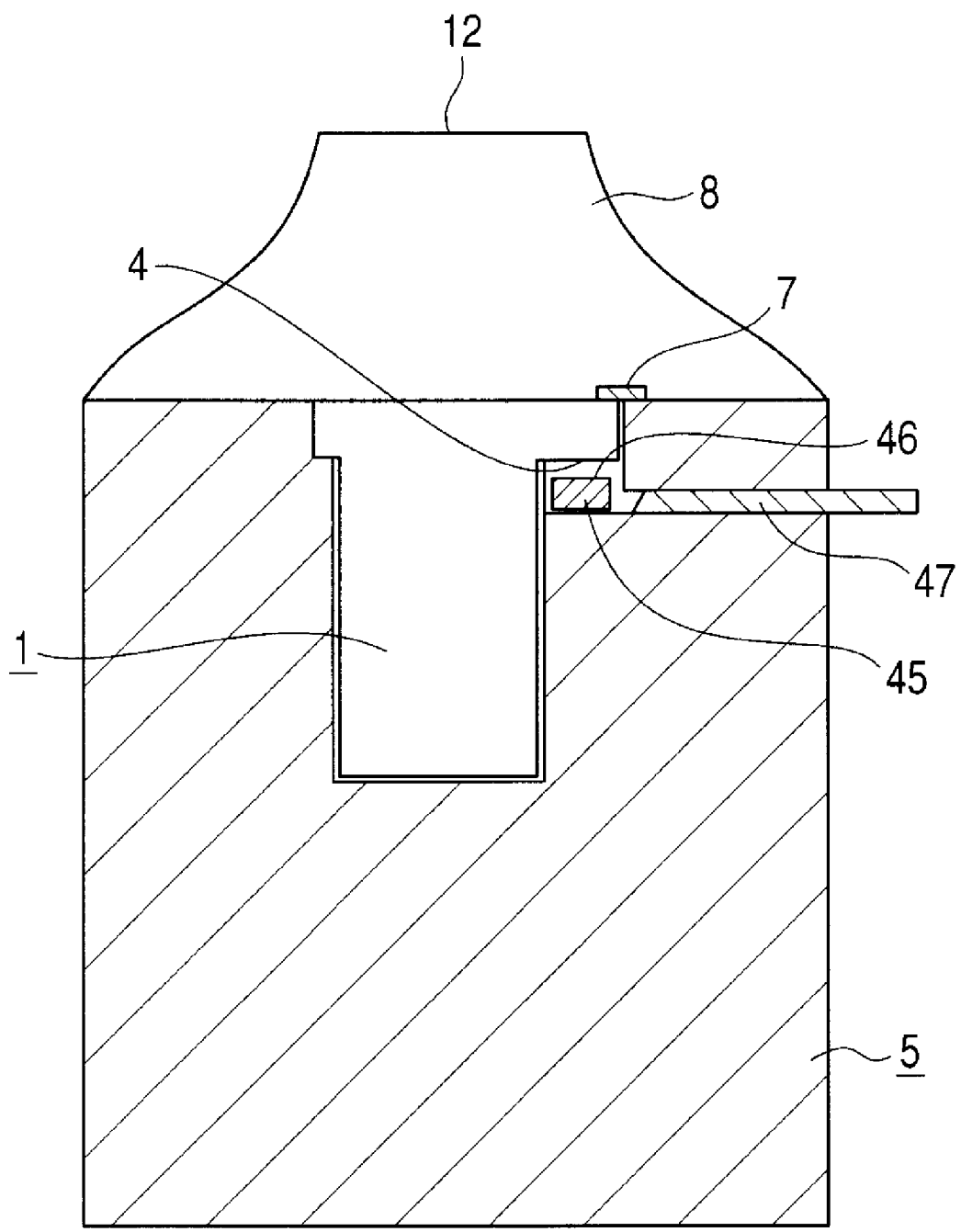
FIG. 11 is a schematic cross-sectional view of the third embodiment of inhaler according to the present invention in a state where electric connection is established.
Figure 12:
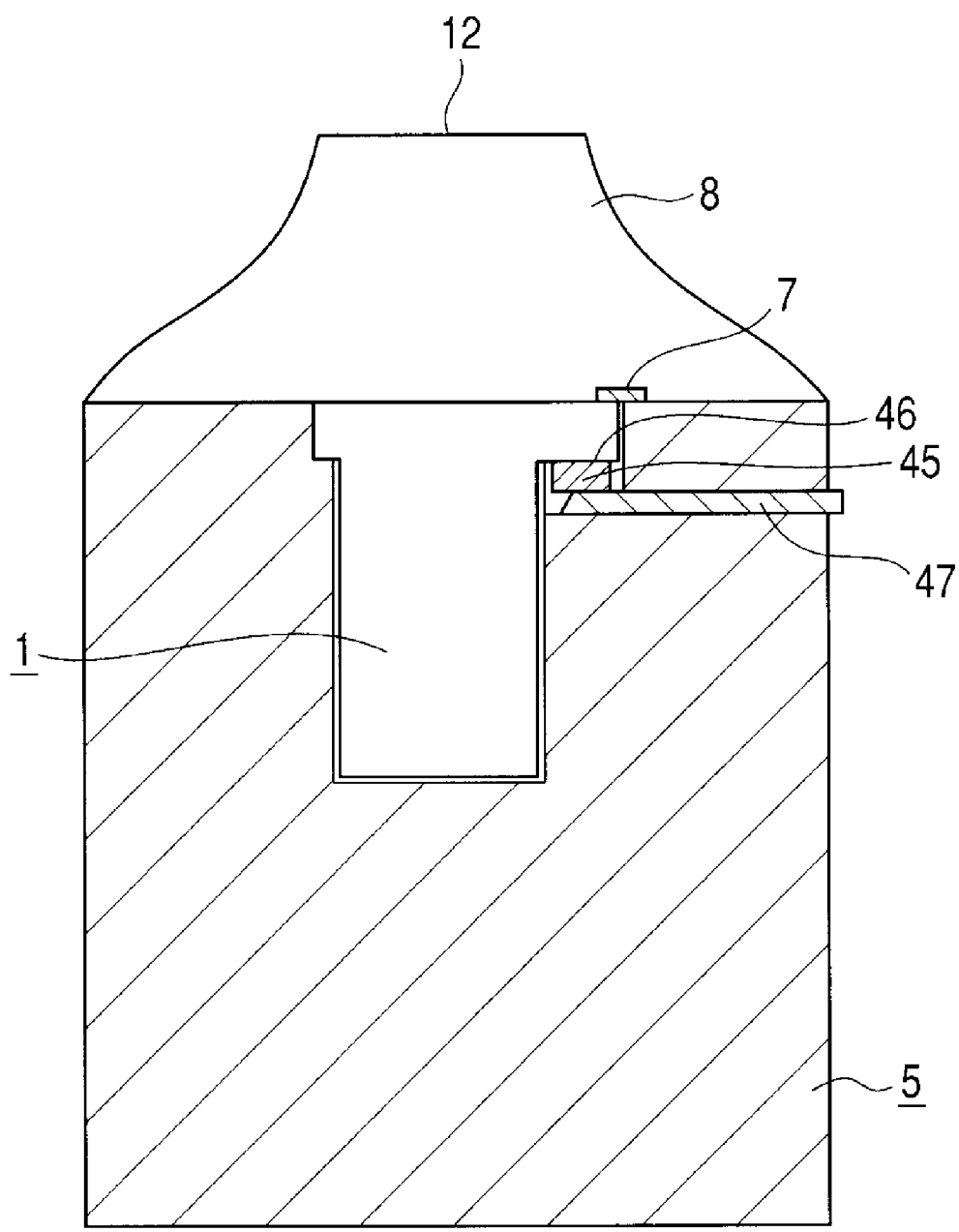
FIG. 12 is a schematic cross-sectional view of the third embodiment of inhaler in a state where electric connection is released.

FIGS. 11 and 12 schematically illustrate the third embodiment of inhaler according to the present invention. The inhaler of this embodiment is provided with a junction forming member (junction forming section) 45 that is movable relative to the inhaler body 5 so as to make it possible to release the electric connection between the cartridge 1 and the inhaler body 5 without removing the inhalation piece 8 and the cartridge 1. With this arrangement, the electric connection between the cartridge 1 and the inhaler body 5 can be released to prevent administration of medicine from taking place even while the cartridge 1 is rigidly secured to the inhaler body 5 so as to prevent the inhaler from unintentionally operating by error and improve the safety of the inhaler.

The junction forming member 45 that is movable relative to the inhaler body 5 is provided with a second electric connection section 46 and the second electric connection section 46 at the side of the inhaler body is electrically connected to the first electric connection section 4 at the side of the cartridge by way of a second cartridge fixing member 47 as illustrated in FIG. 12. The electric connection between the cartridge 1 and the inhaler body 5 is released as the cartridge fixing member 47 is moved toward the outside of the inhaler body 5 and the electric connection section 46 is released from the secured position and separated from the first electric connection section 4. To establish electric connection once again, the cartridge fixing member 47 is pushed in to move the first fixing member 45 having the electric connection section 46 upward and bring it into contact with the electric connection section 4 of the cartridge 1. Then, the cartridge 1 is electrically energized.

The present invention is not limited to the above embodiments and various changes and modifications can be made within the spirit and scope of the present invention. Therefore, to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-200448, filed Aug. 4, 2008, which is hereby incorporated by reference herein in its entirety.

What is claimed is:

1. An inhaler for ejecting medicine and causing a user to inhale it, the inhaler comprising:
   a cartridge having an ejection head for ejecting medicine and a reservoir;
   an inhaler body equipped with an inhalation piece having a suction port, and a cartridge mounting section for mounting said cartridge thereon;
   a junction forming section arranged at said cartridge so as to be brought into contact with said cartridge mounting section of said inhaler body;
   a cartridge fixing member for fixing said cartridge on said inhaler body;
   a first electric connection section arranged at said junction forming section of said cartridge; and
   a second electric connection section arranged at said cartridge mounting section of said inhaler body to be held in contact with said first electric connection section in order to supply electric power to said ejection head,
   wherein said cartridge fixing member is adapted to connect said first electric connection section to said second electric connection section and form part of an air flow path for leading the medicine ejected from said ejection head to said suction port by rigidly securing said junction forming section of said cartridge to said cartridge mounting section of said inhaler body.

2. The inhaler according to claim 1, wherein said first electric connection section and said second electric connection section are held touching each other and connected to each other in the direction in which said cartridge is mounted on said inhaler body.

* * * * *